United States Patent [19]

Patipa et al.

[11] Patent Number: 4,644,952
[45] Date of Patent: Feb. 24, 1987

[54] SURGICAL OPERATING INSTRUMENT

[75] Inventors: Michael Patipa, West Palm Beach; Thomas A. McMillan, North Palm Beach; Henry W. Mitchell, Palm Beach Gardens, all of Fla.

[73] Assignee: Palm Beach Medical Engineering, Inc., Teaneck, N.J.

[21] Appl. No.: 702,500

[22] Filed: Feb. 19, 1985

[51] Int. Cl.$^4$ .............................................. A61F 17/32
[52] U.S. Cl. ................................. 128/305; 128/303 R; 173/123
[58] Field of Search ........................... 128/303 R, 305; 173/123, 122, 116, 100, 95

[56] References Cited

U.S. PATENT DOCUMENTS

| | | | |
|---|---|---|---|
| 2,051,053 | 8/1936 | Morris | 173/123 |
| 2,211,741 | 8/1940 | Elwell | 173/123 |
| 2,646,100 | 7/1953 | Gibson | 173/123 |
| 3,280,921 | 10/1966 | Bickford | 173/123 |
| 3,832,776 | 9/1974 | Sawyer | 128/305 |
| 4,246,902 | 1/1981 | Martinez | 128/305 |
| 4,314,560 | 2/1982 | Helfgott et al. | 128/305 |
| 4,320,761 | 3/1982 | Haddad | 128/305 |

Primary Examiner—Robert Peshock
Assistant Examiner—J. Hakomaki
Attorney, Agent, or Firm—Mandeville & Schweitzer

[57] ABSTRACT

A compact surgical operating instrument, including an elongated cylindrical housing supporting a projecting shaft which is mounted for reciprocation by a coaxially arranged cam assembly rotated by a motor drive. The cam assembly includes two continuous, opposed, canted cam surfaces which positively and alternatively drive forwardly and rearwardly a cam follower mounted on the inner end of said shaft, thereby converting rotation of the cam assembly to reciprocal movement of said shaft without the use of return springs.

4 Claims, 6 Drawing Figures

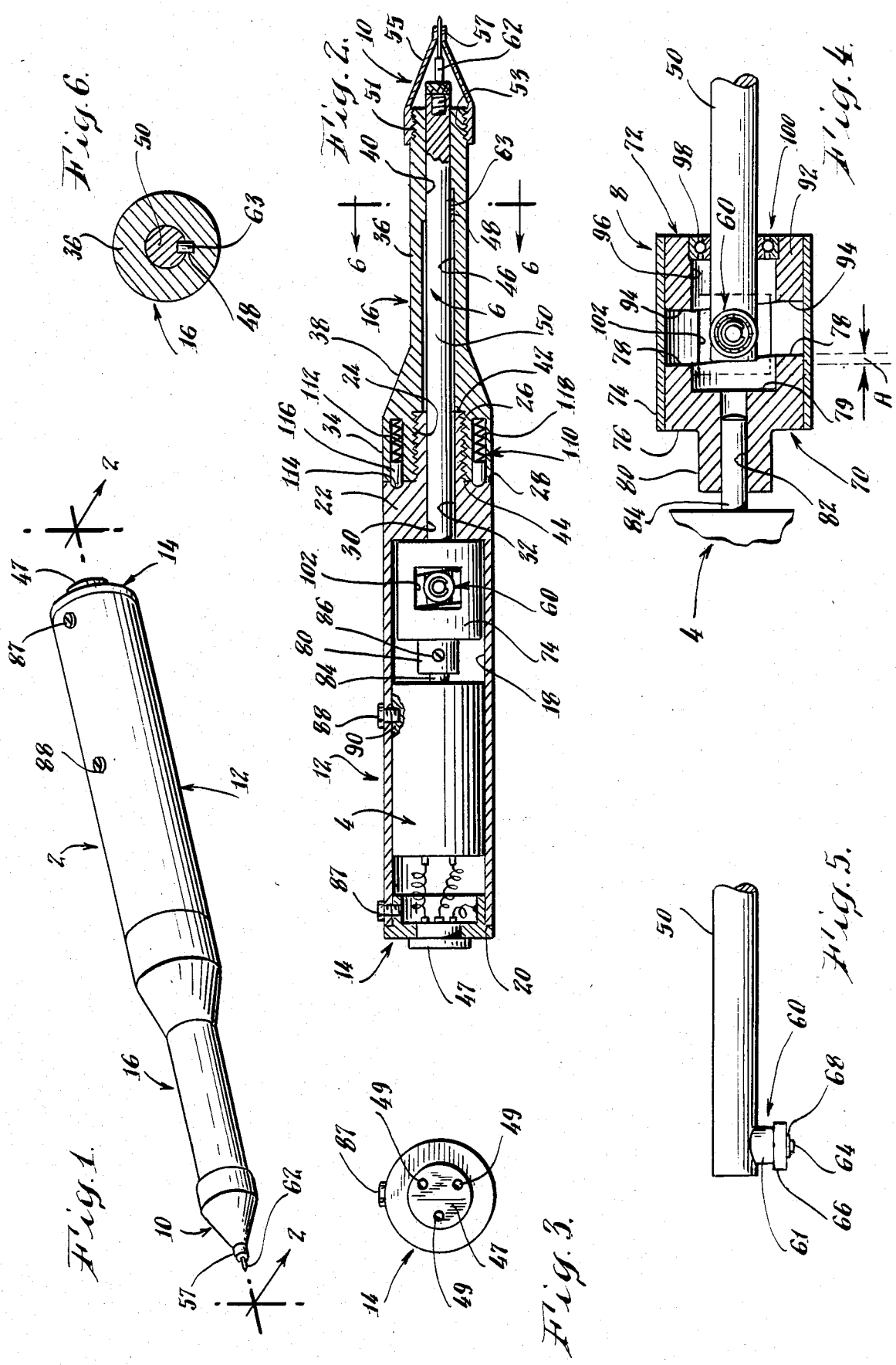

SURGICAL OPERATING INSTRUMENT

TECHNICAL FIELD

This invention relates to an operating instrument having a mechanism for moving an operating device, such as a needle, with a reciprocating motion.

BACKGROUND ART

While operating instruments have been made in the past having a reciprocating shaft for reciprocal movement of a needle or tool, no disclosure was found having the construction of the present invention. Prior art uncovered is listed below: U.S. Pat. Nos. 464,801; 4,031,783; 4,204,438; and 4,246,902.

DISCLOSURE OF INVENTION

An object of the present invention is to provide an instrument having a new and improved mechanism for the reciprocation of an operating device, said mechanism providing cams for positive forward and rearward movement of a reciprocating shaft, without the use of a spring return in one direction.

Another object of the present invention is to provide a rotating cam assembly for transferring its rotative movement to reciprocal movement of an operating shaft; an operating shaft has a cam follower at one end positioned radially outwardly between two cam surfaces which reciprocate the operating shaft.

A further object of the present invention is to provide a cam assembly having two cam members spaced apart and fixed in a sleeve with two continuous cam surfaces facing each other; a bore extends through one cam member to place the end of a shaft therethrough; a short shaft extends radially from the end of said shaft with a cam follower mounted thereon to engage both continuous cam surfaces; rotation of the matching cam surfaces control reciprocal movement of the shaft.

Another object of the present invention is to provide for covering or uncovering a part of the operating device, or needle, during an operation to obtain a desired outward exposure of the operating device, or needle.

BRIEF DESCRIPTION OF THE DRAWINGS

FIG. 1 is a perspective view of the surgical operating instrument;

FIG. 2 is a longitudinal cross-sectional view, taken along line 2—2 of FIG. 1, of the surgical operating instrument showing the electric motor, reciprocating shaft assembly and connecting rotating cam assembly;

FIG. 3 is a rear end view of the surgical operating instrument shown in FIG. 1;

FIG. 4 is an enlarged sectional view of the cam assembly, with the cooperating rear end of the reciprocating shaft assembly and drive shaft of the electric motor shown in full;

FIG. 5 is a view of the rear end of the reciprocating shaft assembly shown in FIG. 4; and FIG. 6 is a view taken on the line 6—6 of FIG. 2 showing the key in the shaft in a keyway in a bore of the main housing.

BEST MODE FOR CARRYING OUT THE INVENTION

A surgical operating instrument according to the present invention is shown in FIG. 1. The surgical operating instrument comprises five main parts: (1) a main housing 2; (2) an electric motor 4; (3) a reciprocating shaft assembly 6; (4) a rotating cam assembly 8; and (5) an operating needle cover 10.

The main housing 2 includes a center cylindrical section 12, a rearward end cap 14, and a forward reciprocating shaft support section 16. The center cylindrical section 12 has an inner longitudinal bore 18 extending fromt he rearward end, where it forms an open end 20, to a point adjacent the forward end, where an integral closed end 22 is formed. A cylindrical axial projection 24 of reduced diameter extends forwardly of the integral closed end 22 of the center cylindrical section 12, said cylindrical axial projection 24 having external threads 26 for a purpose to be hereinafter described. A forwardly facing annular surface 28 is formed on the outside of the integral closed end 22 between the external threads 26 and the outer edge of the center cylindrical section 12. An axial bore 30 extends through the integral closed end 22 and cylindrical axial projection 24, said axial bore 30 having a longitudinal keyway 32 along its entire length.

The forward reciprocating shaft support section 16 has a rearward short cylindrical surface 34 having the same diameter as the center cylindrical section 12, a forward elongated cylindrical surface 36 of reduced diameter, and a connecting conical surface 38. An opening 40 extends axially through the forward reciprocating shaft support section 16.

The rearward part of the opening 40 is enlarged at 42 and internally threaded to receive the external threads 26 of cylindrical axial projection 24. A rearwardly facing annular surface 44 is formed at the rearward end of the rearward short cylindrical surface 34. The rearwardly facing annular surface 44 will face forwardly facing annular surface 28 when external threads 26 of cylindrical axial projection 24 threadably engage the internally threaded forward part 42 of the opening 40. The cylindrical axial projection 24 is shorter than the forward part 42 of the opening 40 to permit the annular surface 44 to meet the annular surface 28.

The opening 40 extends from the rear end of enlarged forward part 42 having an elongated part 46 with a diameter which includes the depth of the longitudinal keyway 32 of axial bore 30, to a point about 2.54 cm (1 inch) from the forward end of the forward reciprocating shaft support 16. The opening 40 extends the remaining 2.54 cm (1 inch) having a diameter equal to the diameter of axial bore 30 and has a longitudinal keyway 48 extending about 0.635 cm ($\frac{1}{4}$ inch) from the rearward end of the elongated part 46, for a purpose to be hereinafter described.

The reciprocating shaft assembly 6 has a reciprocating shaft 50 with a cam follower mechanism 60 mounted on its rearward end, an operating needle 62 mounted on its forward end, and a pin 63 projecting from the side thereof adjacent the forward end forming a key. While operating needle 62 is shown threaded into the end of reciprocating shaft 50, it can be attached by other known means. It can be seen that the reciprocating shaft 50 when it is positioned in the center cylindrical section 12 and forward reciprocating shaft support section 16, has a sliding fit with axial bore 30 and the rear portion of the opening 40 which is formed having the diameter of axial bore 30. The pin, or key, 63 is positioned in the keyway 48 preventing rotation of the shaft 50. The cam follower mechanism 60 is located in the forward part of the inner longitudinal bore 18, and the forward end of the reciprocating shaft 50, with the operating needle 62, is projecting from the forward end of the forward reciprocating shaft support section 16. The forward end of the reciprocating shaft support section 16 is externally threaded at 51 to receive internal threads 53 at the rearward end of the operating needle cover 10. The needle cover tapers forwardly and inwardly from the internal threads 53, as a conical member 55, to a point along the length of the operating needle 62, where a short cylindrical member 57 surrounds the needle 62 and acts as a guide, leaving a desired needle 62 projection. Cam follower mechanism 60 comprises a short shaft 61 extending 90° from the rear end of reciprocating shaft 50 with a projecting axle member 64 having a bearing 66 mounted thereon. A snap ring 68 holds the inner race of the bearing 66 on the axle member 64.

Rotating cam assembly 8, see FIG. 2, is formed having a rearward cam member 70 and forward cam member 72 fixedly mounted in a cage sleeve 74; cage sleeve 74 having a diameter smaller than the inner longitudinal bore 18 so that it can be positioned in the forward part thereof for rotation. While these three parts have been brazed together, they may be fixed by other means, or formed as an integral unit. The rearward cam member 70 has a short cylindrical portion 76 with its forward end comprising a cam face 78 around its outer portion extending inwardly at approximately 90° to the inner surface of cage sleeve 74, and a central bore 79. A rearward axial projection 80 extends from its rearward end and has a bore 82 therein extending to a large diameter bore 79 to receive a drive shaft 84 of the electric motor 4. A set screw 86 in the axial projection 80 screws into the drive shaft 84 of the electric motor 4 so that the electric motor 4 can rotate the rotating cam assembly 8. Electric motor 4 is fixedly positioned in the inner longitudinal bore 18 rearwardly of the rotating cam assembly 8. Set screws 88 extend through the center cylindrical section 12 into the housing 90 of the electric motor 4. Rearward end cap 14 fits in open end 20 of cylindrical section 12 and is held therein by a set screw 87. Located in an opening through the center of the end cap 14 is an electrical jack 47 having three openings 49 adapted to receive a three-prong plug from a power source, and earth ground, not shown. Two openings 49 have contacts connected to the motor 4 to power it, and one opening 49 is for the provision of a ground.

The forward cam member 72 has a short cylindrical portion 92 with its rearward end comprising a cam face 94 around its outer portion extending inwardly at approximately 90° to the inner surface of cage sleeve 74, and a large diameter bore 96 extending axially therethrough to receive the rearward end of the reciprocating shaft 50. Large diameter bores 79 and 96 aid in assembly of the reciprocating shaft assembly 6 within the formed cam assembly 8. The forward end of the large bore 96 intersects a short larger diameter bore 98 in the forward surface of the short cylindrical portion 92 and forms an annular step where the bores 96 and 98 meet; the outer race of a bearing 100 being fixed in said annular step with the inner race being mounted for small sliding movement with reciprocating shaft 50. In assembly of the reciprocating shaft assembly 6, the inner race of bearing 100 can be placed over reciprocating shaft 50 before the pin 63 is fixed in place. The pin 63 is shown fixed in a hole reciprocating shaft 50 (see FIG. 6). An opening 102 is placed in each side of the cage sleeve 74 to aid in the spacing of the cam faces 78 and 94, when the cam members 70 and 72 are being fixed to the cage sleeve 74, and in assembly of the surgical operating instrument. Cam faces 78 and 94 are equally spaced from each other and spaced to permit a proper operating dimension for the outer periphery of the bearing 66 as the cam faces 78 and 94 actuate it.

The cam faces 78 and 94 form one continuous channel between them. This channel has a forward slant from a rearwardmost position (see top of FIG. 4) located towards the motor 4 (rearward part of operating instrument) to a diametrically opposed forwardmost position (see bottom of FIG. 4) located towards the operating needle 62 (forward part of operating instrument) and has a rearward slant back again to the rearwardmost position, with smooth transition between reversing forward and rearward slants. As the cam assembly 8 rotates the cam face 78, the portion of the cam face 78 from the rearwardmost position to the forwardmost position contacts cam follower mechanism 60 and moves the reciprocating shaft 50 forwardly the distance A between the rearwardmost position and forwardmost position (see FIG. 4); the portion of the cam face 94 from the forwardmost position to the rearwardmost position contacts cam follower mechanism 60 and moves the reciprocating shaft 50 rearwardly the distance A between the forwardmost position and rearwardmost position. The length of movement of the reciprocating shaft 50 can be changed by moving the location of the forwardmost position or rearwardmost position of the channel in a forward or rearward direction when forming the cam assembly 8. While one method of forming the cam assembly 8 has been disclosed, other methods can be used.

If it is desired to have the reciprocating shaft 50 move faster in one direction than the other, the relation of the rearwardmost position and forwardmost position around the continuous channel can be changed, making one slant, or ramp, longer than the other. If the forward slant, or ramp, is made short, the reciprocating shaft 50 will move forwardly faster than rearwardly, and if the rearward slant, or ramp, is made short, the reciprocating shaft 50 will move rearwardly faster than forwardly.

It can be seen that as the cylindrical section 12 is rotated in relation to the forward reciprocating shaft support section 16, the needle cover 55 will move along the operating needle 62, varying the amount of exposed needle. A mechanism 110 has been placed between the forwardly facing annular surface 28 and the cooperating rearwardly facing annular surface 44 to hold the cylindrical section 12 and the reciprocating shaft support section 16 in a desired rotated position to obtain a desired operating needle 62 exposure for an operation.

This mechanism 110 includes the location of four (4) cylindrical bores 112 equally spaced around the rearwardly facing annular surface 44 extending into the reciprocating shaft support section 16, and four (4) indentations, or shallow rounded dents, 114, equally spaced around the forwardly facing annular surface 28; said shallow dents 114 and cylindrical bores 112 being aligned at every one-quarter (¼) turn of the cylindrical section 12 with respect to the reciprocating shaft support section 16. A pin 116, having a rounded end and a length of approximately one-third (⅓) of the depth of a cylindrical bore 112, is placed in each cylindrical bore 112, with a spring 118 being placed between each pin 116 and bottom of its cooperating cylindrical bore 112. Each spring 118 forces the rounded end of its pin 116 against the forwardly facing annular surface 28, and when the shallow rounded dents 114 are aligned with the cylindrical bores 112, the rounded end of each pin 116 is forced into a mating shallow rounded dent 114, holding the cylindrical section 12 and the reciprocating shaft support section 16 in that position.

We claim:

1. A compact surgical operating instrument comprising
   (a) a generally cylindrical elongated housing an axial bore therein;
   (b) a shaft mounted in said housing for limited axial reciprocable movement, the forward end of said shaft projecting outwardly through said bore;
   (c) a hollow cylindrical cam assembly mounted in said housing in coaxial relation with said shaft for rotation about said shaft;
   (d) drive housing for rotating said cam assembly;
   (e) the rearward end of said shaft being connected to said cam assembly;
   (f) said cam assembly having spaced, opposed forward and rearward continuous cam surfaces;
   (g) said forward cam surface having an opening therethrough;
   (h) the rearward end of said shaft extending through the opening of said forward cam surface;
   (i) cam follower means mounted on the rearward end of said shaft and being positioned between said facing cam surfaces;
   (j) said cam follower being displaced axially of said housing by said cam surfaces to convert rotating movement of said cam assembly to reciprocal movement of said shaft.

2. The operating instrument of claim 1, in which
   (a) said spaced cam surfaces are mounted in a cage sleeve;
   (b) one of said cam surfaces including center bore to receive said rearward end of said shaft therethrough;
   (c) said cam surface being disposed in oppositely canted, parallel places which intersect the longitudinal axis of said shaft.

3. The surgical instrument of claim 1, in which
   (a) said cam follower is in the form of a roller bearing;
   (b) said bearing having an inner race fixed to said shaft;
   (c) said bearing having an outer rotatable surface mounted between said two cam surfaces;
   (d) one cam surface displacing said shaft in a first direction and
   (e) the other cam surface displacing said shaft in the opposite direction, thereby reciprocating said shaft.

4. The operating instrument of claim 3, in which
   (a) said cam surfaces are spaced a predetermined distance equal to the diameter of said roller bearing.

* * * * *